United States Patent [19]
Miser

[11] Patent Number: 5,939,457
[45] Date of Patent: Aug. 17, 1999

[54] METHOD FOR REDUCING SKIN WRINKLES AND REGULATING SKIN ATROPHY

[75] Inventor: Daniel A. Miser, Provo, Utah

[73] Assignee: Nu Skin International, Inc., Provo, Utah

[21] Appl. No.: 08/957,149

[22] Filed: Oct. 24, 1997

[51] Int. Cl.⁶ ...................................................... A61K 7/48
[52] U.S. Cl. ........................... 514/557; 514/568; 514/844; 514/873
[58] Field of Search ..................................... 514/557, 844, 514/873, 568

[56] References Cited

U.S. PATENT DOCUMENTS 5,422,370  6/1995  Yu et al. .
5,547,988  8/1996  Yu et al. .
5,573,759  11/1996  Blank ......................................... 424/60
5,616,332  4/1997  Herstein ................................... 424/401

*Primary Examiner*—Rebecca Cook
*Attorney, Agent, or Firm*—Thorpe, North & Western, LLP

[57] ABSTRACT

A method for reducing signs of aging in human skin. The method includes the steps of (a) topically applying to the skin a hydroxy acid product having at most a hydroxy acid concentration of approximately 7.0% and having a pH range of between 3 and 4 which causes an increase in exfoliation of the skin; (b) topically applying to the skin a non-hydroxy acid product; (c) repeating steps (a) and (b) at least twice daily for approximately four weeks; and (d) repeating only step (b) at least twice daily for approximately another 4 weeks.

9 Claims, No Drawings

METHOD FOR REDUCING SKIN WRINKLES AND REGULATING SKIN ATROPHY

BACKGROUND OF THE INVENTION

1. The Field of the Invention

This invention relates generally to skin care products, and more particularly to a method by which wrinkles in the skin are smoothed.

2. The Background Art

It is known in the art to use hydroxy acid products to treat human skin. Hydroxy acids are known to "alleviate or improve skin lines; blotches; blemishes; nodules; wrinkles; pigmented spots; atrophy; precancerous lesions; elastotic changes characterized by leathery, coarse, rough, dry and yellowish skin; and other skin changes associated with intrinsic aging or skin damages caused by extrinsic factors such as sunlight, radiations, air pollution, wind, cold, dampness, heat, chemicals, smoke and cigarette smoking." See U.S. Pat. No. 5,547,988 (Yu et al).

Hydroxy acids are effective because the human skin has an inherent (but weak) buffering system that is easily overcome by hydroxy acid formulations that are available over the counter. These formulations have the desired concentration range of hydroxy acids and pH range of products that are intended for unsupervised home use. The mechanism of action for hydroxy acids is not completely understood, but it is known that to be effective in increasing basal cell renewal rates and to be effective in increasing exfoliation times in a cosmetic formulation, the hydroxy acid formulation itself needs to be at a pH of less than 4.0 regardless of the acid concentration. Hydroxy acid formulations with a pH of less than 3.0 may be effective, but should not be considered for unsupervised home use and formulations with a pH higher than 4.0 will generally have little if any effect on skin physiology. Once the hydroxy acid formulation contacts the skin there is an almost immediate yet transient decrease in skin pH. The amount of time (anywhere from 20 minutes to 2 hours) that skin pH is lowered below the normal range of 4.5 to 6.0 will vary from person to person.

In 1997, the Food and Drug Administration (FDA) published its findings on the safety of alpha hydroxy acid products. To summarize, the FDA declared alpha hydroxy acid products safe for unsupervised use at concentrations of no more than 10% and at a pH of no less than 3.5. However, it may be possible to use products containing 10% or more acids when the products in this concentration range are generally at a pH of less than 3.0. Furthermore, products containing 10% or more acids can be used continuously with continued benefits to the skin. However, these products are more likely to cause problems for the user, i.e., burning, stinging, erythema, irritation, etc. The acids making up the 10% concentration are glycolic and lactic.

It is well known that human skin will stop or be slower in responding to cell renewal stimulation after 4 to 8 weeks of continued use of topically applied hydroxy acids. The skin gradually strengthens its buffering system to adapt to the daily assault from hydroxy acids so that any effect the acids have on skin physiology is eventually nullified. To regain the buffering system that allows for beneficial cell renewal stimulation, the skin should be allowed to rest from hydroxy acid use for a period of 4 to 6 weeks. This rest allows the buffering system to return to normal and the process can be started again.

A significant problem of the prior art is that most of the improvements in the skin condition that are made through the hydroxy acid treatments in the first 4 to 8 weeks are lost during the rest period in the next 4 to 6 weeks. During the rest period, the skin tends to return to its original state so that when the buffering system returns to normal the beneficial effects that were realized in the skin during the first 4 to 8 weeks are no longer apparent. The cell renewal stimulation process is once again at or very near the original state of the skin.

The '988 (Yu et al) patent teaches a method for improving the skin condition of a human. Although the '988 patent does not mention a particular pH to be used in the hydroxy acid formulation, the patent mentions a formulation containing at least a 5.0% concentration of hydroxy acid or its derivative. In fact, the '988 patent teaches that the hydroxy concentration is "preferably between 8 to 20%." Column 14, lines 28–30. In addition, the '988 patent teaches that "Blotches, blemishes, nodules, age spots, pigmented spots, skin lines, and fine wrinkles improved or disappeared" three to five months after the recommended treatment. Column 15, lines 39–42. The '988 patent also teaches application of the hydroxy acid product on a daily basis without rest periods for the skin. Column 18, lines 17–18.

Yu et al are the inventors of another related invention described in U.S. Pat. No. 5,422,370 (the '370 patent). The '370 patent teaches a method to improve dry and flaky skin using a product having 3% to 7% hydroxy acids. Column 15, lines 52–64. The '370 patent does not teach a specific amount of topical lotion to be applied nor a specific time period for which the lotion should be applied. See column 20, lines 52–56. The length of time the lotion is applied is indefinite, being stated as one to three weeks for improvements in age spots (column 18, line 29), one to three months for substantial eradication of age spots (column 18, lines 30–31), and two to four months for complete eradication of age spots (column 18, lines 33–35). The '370 patent also states that a composition with a 10% to 20% concentration of hydroxy acids is preferable when treating wrinkles but that favorable results do not occur within four months of time. Column 18, lines 35–43. The '370 patent does not disclose alternating hydroxy acid use with rest periods for improvements in skin condition.

Of current interest is a cell renewal stimulation process that preserves skin improvements that are realized through treatments with hydroxy acid products when the use of the hydroxy acid products is alternated with a rest period.

OBJECTS AND SUMMARY OF THE INVENTION

It is an object of the present invention to provide a system for reducing the signs of aging in human skin through the use of hydroxy acid and non-hydroxy acid products.

It is another object of the invention to provide such a system that may be cyclically repeated over a period of approximately two months and therein maintain improvements in skin condition throughout the cycle.

It is also an object of the present invention to provide such a system for reducing wrinkles in the human skin.

It is a further object of the present invention to provide such a system for alleviating skin blemishes, nodules, pigmented spots, atrophy, and precancerous lesions.

It is still another object of the present invention to provide such a system for alleviating elastotic changes in the skin such as leathery, coarse, rough, dry, and yellowish skin.

It is an additional object of the present invention to provide such a system for counteracting the detrimental effects on the skin caused by sunlight, wind, cold air, pollution, chemicals, and other hazards that may be encountered by the skin.

It is yet another object of the invention, in accordance with one aspect thereof, to provide a system for alleviating signs of aging through topically applying a hydroxy acid product and a non-hydroxy acid product.

It is still another object of the invention, in accordance with another aspect thereof, to provide a system for alleviating signs of aging in the skin of the face and neck.

The above objects and others not specifically recited are realized through a method for reducing signs of aging in human skin. The method includes the steps of (a) topically applying to the skin a hydroxy acid product having at most a hydroxy acid concentration of 7.0% and having a pH range of between 3 and 4 which causes an increase in exfoliation of the skin; (b) topically applying to the skin a non-hydroxy acid product for tightening and firming the skin; (c) repeating steps (a) and (b) at least twice daily for approximately four weeks; and (d) repeating only step (b) at least twice daily for approximately another 4 weeks.

It is an advantage of the present invention to provide a system for reducing the signs of aging in human skin through the use of both hydroxy acid and non-hydroxy acid products so that a method of the system may be cyclically repeated over a period of approximately two months while improvements in skin condition are maintained throughout the cycle.

It is also an advantage of the present invention to provide such a system for reducing wrinkles in human skin on the face and neck, for alleviating skin blemishes, nodules, pigmented spots, atrophy, and precancerous lesions, for alleviating elastotic changes in the skin such as leathery, coarse, rough, dry, and yellowish skin, and for counteracting the detrimental effects on the skin caused by sunlight, wind, cold air, pollution, chemicals, and other hazards that may be encountered by the skin.

Additional objects and advantages of the invention will be set forth in the description which follows, and in part will be apparent from the description, or may be learned by the practice of the present invention. The objects and advantages of the invention may be realized and obtained by means of the instruments and combinations particularly pointed out in the appended claims.

DETAILED DESCRIPTION

The invention will be discussed so as to enable one skilled in the art to make and use the invention. It is to be understood that the following description is only exemplary of the principles of the present invention, and should not be viewed as narrowing the appended claims.

As used herein, "hydroxy acid" refers to 2-hydroxy carboxylic acids and related compounds, and mixtures thereof. U.S. Pat. No. 5,422,370, both to Yu et al., are hereby incorporated by referenced because of the detail with which such hydroxy acids are described. Preferred hydroxy acids include lactic acid, citric acid, and salicylic acid and mixtures thereof.

As used herein, a "hydroxy acid product" refers to a topical skin care product useful for reducing signs of aging of skin and for smoothing rough and/or dry skin comprising an effective amount of a hydroxy acid or mixture of hydroxy acids with the provision that such hydroxy acid or mixture of hydroxy acids is present at a concentration no greater than 7% by weight.

As used herein, a "non-hydroxy acid product" means a topical skin care product for tightening and firming the skin that does not contain an effective amount of a hydroxy acid.

As used herein, "effective amount" means an amount of a hydroxy acid or mixture thereof sufficient to reduce the signs of aging in human skin and to smooth rough and/or dry skin when used according to the reading of the present disclosure. A person of ordinary skill in the art can determine such effective amount for any particular hydroxy acid or mixture of hydroxy acids without undue experimentation by applying the guidelines set forth herein. An effective amount of a hydroxy acid product or a non-hydroxy acid product is an amount that can be rubbed into the skin within a few minutes.

The hydroxy acid product and non-hydroxy acid product can be formulated as a solution, gel, lotion, cream, ointment, or other cosmetically acceptable form according to principles well known in the art.

The present invention is a cell renewal stimulation process that preserves skin improvements that are realized through treatments with hydroxy acid products. The invention provides a method for preserving the skin improvements made during hydroxy acid treatment when the hydroxy acid products are discontinued to provide a rest period for the skin. The hydroxy acid products are for reducing signs of aging in human skin and, if the products are used in accordance with the principles of the present invention, the benefits to the skin that are realized during hydroxy acid treatment periods will not be lost during periods when the hydroxy acid treatment is discontinued for the skin buffering system to rejuvenate.

The method of the present invention is preferably preceded by cleaning the skin to be treated in the method. Usually, the skin to be treated is on the neck and face, but not the eyelids. Cleaning the skin includes performing personal hygiene techniques that are common to the ordinary person.

After proper cleansing of the treatment skin, a hydroxy acid product having at most a hydroxy acid concentration of approximately 7.0% (preferably a maximum of 5.0% for the face and neck) and having a pH range of between 3 and 4 will be topically applied to the skin. This hydroxy acid product causes an increase in exfoliation of the skin by influencing a basal cell renewal rate and loosening intercellular bonds of keratinocytes. The next step in the method is topically applying to the skin a non-hydroxy acid product having a mixture of botanical extracts for tightening and firming the skin. The botanical extracts commonly include Hydrocotyl Extract, Coneflower Extract, water, emulsifiers, preservatives, and fragrance.

The emulsion systems could have numerous ingredient variations. The following examples demonstrate embodiments of the emulsion systems of the present invention.

| Ingredients | % (W/W) |
| --- | --- |
| Example 1 | |
| Mineral Oil | 15.0 |
| Oleth-5 | 9.0 |
| DEA Oleth-3 Phosphate | 6.0 |
| Water | 50.0 |
| Acetamide MEA (and) Lactamide MEA | 1.0 |
| Propylene Glycol | 12.0 |
| Glycerin | 7.0 |

-continued

| Ingredients | % (W/W) |
|---|---|
| Example 2 | |
| Water | 86.0 |
| Emulsifying Wax NF | 6.0 |
| Behentrimonium Methosulfate (and) Cetearyl Alcohol | 3.0 |
| Mineral Oil | 4.0 |
| Preservative | 1.0 |
| Example 3 | |
| Water | 85.0 |
| Stearic Acid | 1.8 |
| Propylene Glycol Stearate S.E. | 2.5 |
| Cetearyl Alcohol (and) Ceteareth-20 | 2.5 |
| Butylene Glycol | 2.0 |
| Diisopropyl Adipate | 2.0 |
| Ethoxydiglycol | 3.0 |
| Preservative | 1.2 |

In addition to the above examples, the Merck Index contains numerous combinations of substances that could be used in the method of this invention. The Merck Index is an encyclopedia of chemicals, drugs, and biologicals. Similar information can also be found in the "Merck Manual" which is available online on the Internet.

The prior two steps (following the optional cleansing of the skin) are repeated for approximately 4 to 6 weeks and then only the step of applying the non-hydroxy acid product is repeated for approximately another 4 to 6 weeks. This second 4 to 6 weeks allows the skin to rest from treatment with the hydroxy acid product while a buffering system in the skin returns to normal. The process is advantageous because the improvements in the skin that are realized through treatment with the hydroxy acid product are not lost during the rest period.

As understood by those skilled in the art, the skin has a buffering system that gradually adjusts to the assaults through applications of the hydroxy acid product. Eventually, any beneficial effect that the acids have on skin physiology is nullified because the buffering system will become strong enough to withstand the assault from the hydroxy acids and the beneficial cell renewal stimulation will cease. Although, initially, the hydroxy acid treatment causes improvements in the skin, the improvements will eventually cease and the hydroxy acid treatment must be discontinued so that the buffering system can return to normal and treatment with the hydroxy acids will again produce improvements in the skin.

When treatment with the hydroxy acids is discontinued, the treatment with the non-hydroxy acid product is continued to preserve the improvements in the skin that were realized through hydroxy acid treatment. This "only non-hydroxy treatment" is continued for approximately four weeks until the buffering system returns to normal. When the buffering system returns to normal, continued treatment with both the hydroxy acid product and the non-hydroxy acid product will again be beneficial. This method of treatment with both the hydroxy acid product and the non-hydroxy acid product is an advantage over the prior art because the method solves the problem of how to preserve skin improvements during the skin rest period.

In a preferred embodiment, the hydroxy acid product and the non-hydroxy acid product are topically applied to the skin twice daily; typically, the morning and the evening. The hydroxy acid product applied in the morning may optionally have a sun screen component added and the hydroxy acid product applied in the evening need not have the sun screen component added. The order of application of the hydroxy acid product and the non-hydroxy acid product is irrelevant to obtaining the beneficial results of the treatment.

Preferably, the complete hydroxy acid product is formulated with a mixture of water emulsifiers, fragrance, preservatives, emollients, thickening agents, and hydroxy acid or mixture of hydroxy acids. In one preferred embodiment, a hydroxy acid product is formulated with a maximum of 4.8% lactic acid and approximately 0.2% salicylic acid. The lactic acid and the salicylic acid combine to form the hydroxy acid concentration of 5.0%, which is preferred for treatment of the face and neck. Another preferred embodiment of the hydroxy acid product is formulated with a mixture of emulsifiers, fragrance, preservatives, emollients, approximately 5.8% lactic acid, approximately 1.0% citric acid, and approximately 0.2% salicylic acid to form a 7.0% hydroxy acid product; the 7.0% hydroxy acid concentration resulting from the mixture of lactic acid, citric acid, and salicylic acid. This latter formulation to be used for rough and/or dry skin below the neck, e.g., elbows, knees, and heels.

The non-hydroxy acid product is preferably formulated with a mixture of botanical extracts proven to tighten and firm the skin by helping to increase collagen and elastin formation through fibroblast stimulation. A preferred embodiment of non-hydroxy acid product comprises a mixture of botanical extracts including Hydrocotyl Extract, Coneflower Extract, water, emulsifiers, preservatives, astringents, thickening agents, and fragrance. The functional ingredients of the botanical mixture are (a) the Hydrocotyl Extract, which is also known as Gotu Kola, Centella Asiatica and Asiatic Acid and (b) the Coneflower Extract, which is also known by the Latin name of Echinacea Extract. The remainder of the ingredients in the botanical extract consists primarily of water, emulsifiers, preservatives, and fragrance.

The above method can be repeated indeterminately while the skin condition improves and thereafter while the skin condition remains stable. The method can also be used specifically for reducing wrinkle depth in the treatment skin.

An alternative embodiment of the present invention is a method for smoothing rough and/or dry skin. The method includes topically applying a 7.0% hydroxy acid product to skin below the neck, e.g., elbows, knees, heels.

The hydroxy acid product is applied by rubbing a topical product into the skin with the finger tips. Enough product should be used to completely cover the treatment area of the skin and the product should be rubbed onto the skin until the skin has completely absorbed the topical product. Preferably, this process is completed twice daily with each application being at least four hours apart.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed and desired to be secured by United States Letters Patent is:

1. A method for reducing skin wrinkles in human skin comprising:
   (a) topically applying to the skin an effective amount of a hydroxy acid product having a hydroxy acid concentration of no greater than 7.0% and having a pH range of between about 3 and 4 thereby promoting exfoliation of the skin;

(b) topically applying to the skin an effective amount of a non-hydroxy acid product for reducing said wrinkles;

(c) repeating steps (a) and (b) at least twice daily for approximately four weeks; and (d) thereafter repeating only step (b) at least twice daily for approximately another 4 weeks.

2. The method of claim 1 wherein the hydroxy acid product is applied in the morning and the evening.

3. The method of claim 2 wherein the hydroxy acid product applied in the morning further comprises a sunscreen component.

4. The method of claim 1 wherein the non-hydroxy acid product is applied in the morning and the evening.

5. The method of claim 1 wherein (a) and (b) comprise applying both the hydroxy acid product and the non-hydroxy acid product only to neck skin and to facial skin other than the eyelids.

6. The method of claim 1 wherein said hydroxy acid product further comprises at least one member selected from the group consisting of emulsifiers, fragrance, preservatives, emollients, and thickening agents.

7. The method of claim 6 wherein said hydroxy acid product comprises up to about 4.8% by weight of lactic acid and about 0.2% by weight of salicylic acid.

8. The method of claim 6 wherein said hydroxy acid product comprises about 0.2% by weight of salicylic acid and amounts of lactic acid and citric acid to result in a product comprising about 7% by weight of hydroxy acids.

9. A method for reducing skin wrinkles in human skin comprising:

(a) topically applying to the skin an effective amount of a hydroxy acid product having a hydroxy acid concentration of no greater than 7.0% and having a pH range of between about 3 and 4 to thereby promote exfoliation of the skin;

(b) topically applying to the skin an effective amount a non-hydroxy acid product having a mixture of botanical extracts for tightening and firming the skin comprising hydrocotyl extracts and coneflower extracts;

(c) repeating (a) and (b) at least twice daily for approximately four weeks; and (d) thereafter repeating only (b) at least twice daily for approximately another 4 weeks.

* * * * *